(12) United States Patent
Gelfand et al.

(10) Patent No.: US 7,226,440 B2
(45) Date of Patent: Jun. 5, 2007

(54) METHOD AND DEVICE FOR ACCESSING A PERICARDIAL SPACE

(75) Inventors: Mark Gelfand, New York, NY (US); Howard Levin, Teaneck, NJ (US)

(73) Assignee: G & L Consulting, LLC, New York, NY (US)

( * ) Notice: Subject to any disclaimer, the term of this patent is extended or adjusted under 35 U.S.C. 154(b) by 0 days.

(21) Appl. No.: 11/275,792

(22) Filed: Jan. 30, 2006

(65) Prior Publication Data

US 2006/0173441 A1 Aug. 3, 2006

Related U.S. Application Data

(60) Provisional application No. 60/648,277, filed on Jan. 31, 2005.

(51) Int. Cl.
*A61M 31/00* (2006.01)
*A61M 29/00* (2006.01)

(52) U.S. Cl. .................... 604/509; 604/96.01

(58) Field of Classification Search .............. 604/21, 604/93.01, 96.01, 506, 507, 508, 509, 510; 600/374; 623/2.37
See application file for complete search history.

(56) References Cited

U.S. PATENT DOCUMENTS

| | | | | | |
|---|---|---|---|---|---|
| 4,884,567 | A | * | 12/1989 | Elliott et al. ................ 606/126 |
| 5,269,326 | A | * | 12/1993 | Verrier ........................ 600/374 |
| 5,336,252 | A | * | 8/1994 | Cohen ......................... 607/119 |
| 5,797,870 | A | * | 8/1998 | March et al. ................ 604/506 |
| 5,827,216 | A | * | 10/1998 | Igo et al. ...................... 604/21 |
| 5,840,059 | A | * | 11/1998 | March et al. ................ 604/509 |
| 5,968,010 | A | * | 10/1999 | Waxman et al. ............ 600/500 |
| 6,043,273 | A | * | 3/2000 | Duhaylongsod ............. 514/478 |
| 6,152,141 | A | * | 11/2000 | Stevens et al. ............. 128/898 |
| 6,162,195 | A | * | 12/2000 | Igo et al. ................ 604/164.13 |
| 6,200,303 | B1 | * | 3/2001 | Verrier et al. .............. 604/508 |
| 6,206,004 | B1 | * | 3/2001 | Schmidt et al. ............. 128/898 |
| 6,217,554 | B1 | * | 4/2001 | Green ................... 604/164.01 |
| 6,554,819 | B2 | * | 4/2003 | Reich ......................... 604/508 |
| 6,565,555 | B1 | * | 5/2003 | Ryan et al. .................... 606/18 |
| 6,585,716 | B2 | * | 7/2003 | Altman ....................... 604/509 |
| 6,613,062 | B1 | * | 9/2003 | Leckrone et al. ........... 606/167 |
| 6,666,844 | B1 | * | 12/2003 | Igo et al. .................... 604/115 |
| 6,692,458 | B2 | * | 2/2004 | Forman et al. .......... 604/93.01 |
| 6,709,427 | B1 | * | 3/2004 | Nash et al. ................. 604/508 |
| 6,711,436 | B1 | * | 3/2004 | Duhaylongsod ............... 607/9 |
| 6,890,353 | B2 | * | 5/2005 | Cohn et al. ................ 623/2.37 |

(Continued)

OTHER PUBLICATIONS

Italian researchers say new treatement "cures AF" Medical Industry Week Sep. 6, 2001.*

(Continued)

*Primary Examiner*—Cris Rodriguez
*Assistant Examiner*—Paul Smith
(74) *Attorney, Agent, or Firm*—Nixon & Vanderhye P.C.

(57) ABSTRACT

A method for accessing a pericardial space of a heart of a mammalian patient is disclosed comprising: guiding a catheter through a coronary sinus of the heart and to a cardiac vein; advancing said catheter to a distal segment of the cardiac vein; intentionally puncturing the vein with the catheter to access the pericardial space, and performing a therapy or a diagnostic procedure using the catheter an the puncture in the vein and using the pericardial space.

15 Claims, 5 Drawing Sheets

U.S. PATENT DOCUMENTS

2002/0183841 A1* 12/2002 Cohn et al. ............... 623/2.36
2006/0074397 A1*  4/2006 Shimada .................... 604/509

OTHER PUBLICATIONS

David Spodick, "Direct Therapy for Coronary Disease, Myocardial Disease, and Severe Cardiac Arrhythmias", Clin. Cardiol. vol. 22 (Suppl. I), p. I-1 (1999).

David Spodick, "Microphysiology of the Pericardium in Relation to Intrapericardial Therapeutics and Diagnostics", Clin. Cardiol. vol. 22 (Suppl. I), pp. I-2-I-3 (1999).

Ralph Shabetai, "Function of the Normal Pericardium", Clin. Cardiol. vol. 22 (Suppl. I), pp. I-4-I-5 (1999).

Roger Laham et al., "Therapeutic Myocardial Angiogenesis Using Percutaneous Intrapericardial Drug Delivery", Clin. Cardiol. vol. 22 (Suppl. I), pp. I-6-I-9 (1999).

Hans-Peter Stoll et al., "Pharmacokinetics and Consistency of Pericardial Delivery Directed to Coronary Arteries: Direct Comparison with Endoluminal Delivery", Clin. Cardiol. vol. 22 (Suppl. I), pp. I-10-I-16 (1999).

Bernhard Maisch et al., "Intrapericardial Treatment of Inflammatory and Neoplastic Pericarditis Guided by Pericardioscopy and Epicardial Biopsy-Results from a Pilot Study", Clin. Cardiol. vol. 22 (Suppl. I), pp. I-17-I-22 (1999).

Keith March et al., "Efficient in Vivo Catheter-Based Pericardial Gene Transfer Mediated by Adenoviral Vectors", Clin. Cardiol. vol. 22 (Suppl. I), pp. I-23-I-29 (1999).

Petar Seferovic et al., "Initial Clinical Experience with PerDUCER® Device: Promising New Tool in the Diagnosis and Treatment of Pericardial Disease", Clin. Cardiol. vol. 22 (Suppl. I), pp. I-30-I-35 (1999).

Michael Macris, Minimally Invasive Access of the Normal Pericardium: Initial Clinical Experience with a Novel Device, Clin. Cardiol. vol. 22 (Suppl. I), pp. I-36-I-39 (1999).

Tonya Dickson et al., "Establishment of a Clinically Correlated Human Pericardial Fluid Bank: Evaluation of Intrapericardial Diagnostic Potential", Clin. Cardiol. vol. 22 (Suppl. I), pp. I-40-I-42 (1999).

Kambeez Berenji et al., "Inadvertent Positioning of Pacemaker Leads in the Pericardium", PACE, vol. 26, Oct. 2003, pp. 2039-2041.

Roger Laham et al., "Intrapericardial Delivery of Fibroblast Growth Factor-2 Induces Neovascularization in a Porcine Model of Chronic Myocardial Ischemia", The Journal of Pharmacology and Experimental Therapeutics, vol. 292, No. 2, Copyright © 2000, pp. 795-802.

* cited by examiner

METHOD AND DEVICE FOR ACCESSING A PERICARDIAL SPACE

This application claims the benefit of the filing date of U.S. Provisional Patent Application 60/648,277 filed Jan. 31, 2005.

BACKGROUND OF THE INVENTION

This invention relates to a method for accessing pericardial space of the heart for delivery of medication or other therapy. It also relates to intravascular catheters for accessing the pericardial space of the heart.

The pericardium (also called pericardial sac or pericardial complex) consists of an outer fibrous layer and an inner serous layer. The fibrous pericardium is a flask-shaped, tough outer sac with attachments to the diaphragm, sternum, and costal cartilage. The serous layer is thin and is adjacent to the surface of the heart. For the purpose of this disclosure references to the pericardial membrane mean the fibrous pericardium and references to the pericardial space mean the space between the outer (fibrous) and the inner (serous) layers.

The pericardium serves as a protective barrier from the spread of infection or inflammation from adjacent structures. The distendable pericardial space produced by these layers normally contains approximately 20 cubic centimeters (cc) of fluid with electrolyte and protein profiles similar to plasma. Fluid serves as a lubricant to allow unimpeded motion of the heart inside the sack. Approximately 120 cc of additional fluid can accumulate in the pericardium without an increase in pressure. Further fluid accumulation can result in marked increases in pericardial pressure, eliciting decreased cardiac output and hypotension (cardiac tamponade).

Access to the pericardial space is desirable to provide a variety of cardiac therapies, including delivery of drugs or genetic agents, placement of electrodes, removal or infusion of fluid for diagnostic analysis or therapy, or other purposes. A variety of mechanisms have been developed for accessing the pericardial space, ranging from a simple puncture by a large bore needle to intricate catheter or cannula based systems provided with sealing and anchoring mechanisms.

Access to the pericardial space in the prior art has been disclosed as: piercing the pericardium from outside or inside the heart, and piercing the wall of a heart chamber. Prior mechanisms adapted to access the pericardial space by piercing the heart chamber include U.S. Pat. No. 5,797,870 issued to March et al, which discloses a catheter with a hollow helical needle to pierce the wall of a heart chamber. Particularly in the context of access to the pericardial space via the right atrium, it has been proposed that the transvenous catheter pierce the right arterial wall, as in U.S. Pat. No. 4,946,457 issued to Elliot and that the catheter pierce the right arterial appendage as in U.S. Pat. No. 5,269,326 issued to Verrier. Access to the pericardial space from the exterior of the body, accomplished by passing a cannula or catheter type device through the chest wall and thereafter passing the cannula or catheter through the pericardium into the pericardial space is disclosed in U.S. Pat. No. 5,827,216 issued to Igo, U.S. Pat. No. 5,336,252 issued to Cohen. These methods and mechanisms are not best suited to access the pericardial space without surgery and without piercing the wall of the heart so as to avoid danger of excessive bleeding.

SUMMARY OF THE INVENTION

The inventive method, in one embodiment, comprises accessing the pericardial space with a catheter guided to a coronary sinus and into a coronary (cardiac) vein via the mammalian patient's venous system. The catheter tip is advanced into a smaller distal (distant) branch of the coronary venous tree that can be sacrificed. The distal branch can be occluded with a catheter tip balloon and isolated from the larger coronary venous tree. Fluid can be infused through a catheter lumen to swell and extend the isolated distal branch. A needle or a wire is introduced into the resulting bubble formed by the extended isolated distal branch. An access device such as a needle, wire or catheter pierces the wall of the distal vein branch and enters the pericardial space.

Following the puncture, the distal vein branch can be filled via a catheter with a clotting agent, biologic glue (bioglue) or other sealing material to facilitate termination of bleeding. After the distal branch of the vein is sealed, the balloon can be deflated and the catheter removed if desired. There will be no significant bleeding from the vein into the pericardial space. The access device can be safely left in place with the distal tip of it residing in the pericardial space and the proximal end available for fluid communication with drug delivery devices, to fill pericardial space with flowable material or to drain fluid. A catheter or an electrode lead can be placed this way in the pericardial space and connected to an implantable pump, a pacemaker or an electric stimulator for a variety of applicable therapies.

A method for accessing a pericardial space of a heart of a mammalian patient is disclosed comprising: guiding a catheter through a coronary sinus of the heart and to a cardiac vein; advancing said catheter to a distal segment of the cardiac vein; intentionally puncturing the vein with the catheter to access the pericardial space, and performing a therapy or a diagnostic procedure using the catheter in the puncture in the vein and using the pericardial space. The method may further comprises extending an access device of the catheter through the puncture and into the pericardial space; and delivering a therapy to the pericardial space through the catheter and the puncture, wherein the therapy includes at least one of delivery of drugs or genetic agents to the pericardial space, placement of electrodes into the pericardial space, removal or infusion of fluid from the pericardial space. The method may further comprise permanently sealing the distal segment with the catheter and/or temporary sealing the distal segment by expanding a balloon at a distal end of the catheter and thereafter puncturing the vein. The permanent sealing the distal segment may be by infusion of a bioglue or a clotting agent or delivery of heat or RF energy. The method may comprise expanding an expandable device at a distal section of the catheter to distend the distal segment of the cardiac vein and then extending an access puncturing and into the pericardial space, and thereafter extending an access device from the catheter to'spuncture the vein.

A method for transvenously accessing a pericardial space between a heart and a pericardium in a mammalian patient has been developed, said method comprising: guiding a catheter downstream through a coronary sinus and coronary vein to a region adjacent the pericardial space, and intentionally accessing the pericardial space with the catheter by penetrating the coronary vein, wherein the catheter is inserted into a peripheral vein and guided to the coronary sinus. The method may further comprise sealing the coronary vein, wherein the seal is a temporary seal formed by expanding a distal section of the catheter in the coronary vein or a permanent seal of a distal segment of the coronary vein and the catheter extends to the distal segment and is retracted from the patient after sealing the distal segment. The permanent sealing is achieved with an infusion of a bioglue or a clotting agent or delivery of heat or RF energy.

The method may further comprise extending an access device of the catheter through the puncture and into the pericardial space, and delivering a therapy to the pericardial space through the catheter and the puncture. The therapy may include at least one of delivery of drugs or genetic agents to the pericardial space, placement of electrodes into the pericardial space, removal or infusion of fluid from the pericardial space.

The method may include accessing the pericardial space by extending an access device from the catheter between a serous layer and fibrous layer of a pericardium of the heart. The serous layer and fibrous layers are separated by distending a distal segment of the coronary vein with the catheter, such as using a balloon on the catheter. The vein can be punctured after the layers are separated.

SUMMARY OF THE DRAWINGS

A preferred embodiment and best mode of the invention is illustrated in the attached drawings that are described as follows.

DETAILED DESCRIPTION OF THE INVENTION

For the proposed clinical use, the capability of the preferred embodiment of the invention is to access the pericardial space of the heat to deliver therapy such as drug substances and to install catheters and electrode leads in that space.

Figure 1:
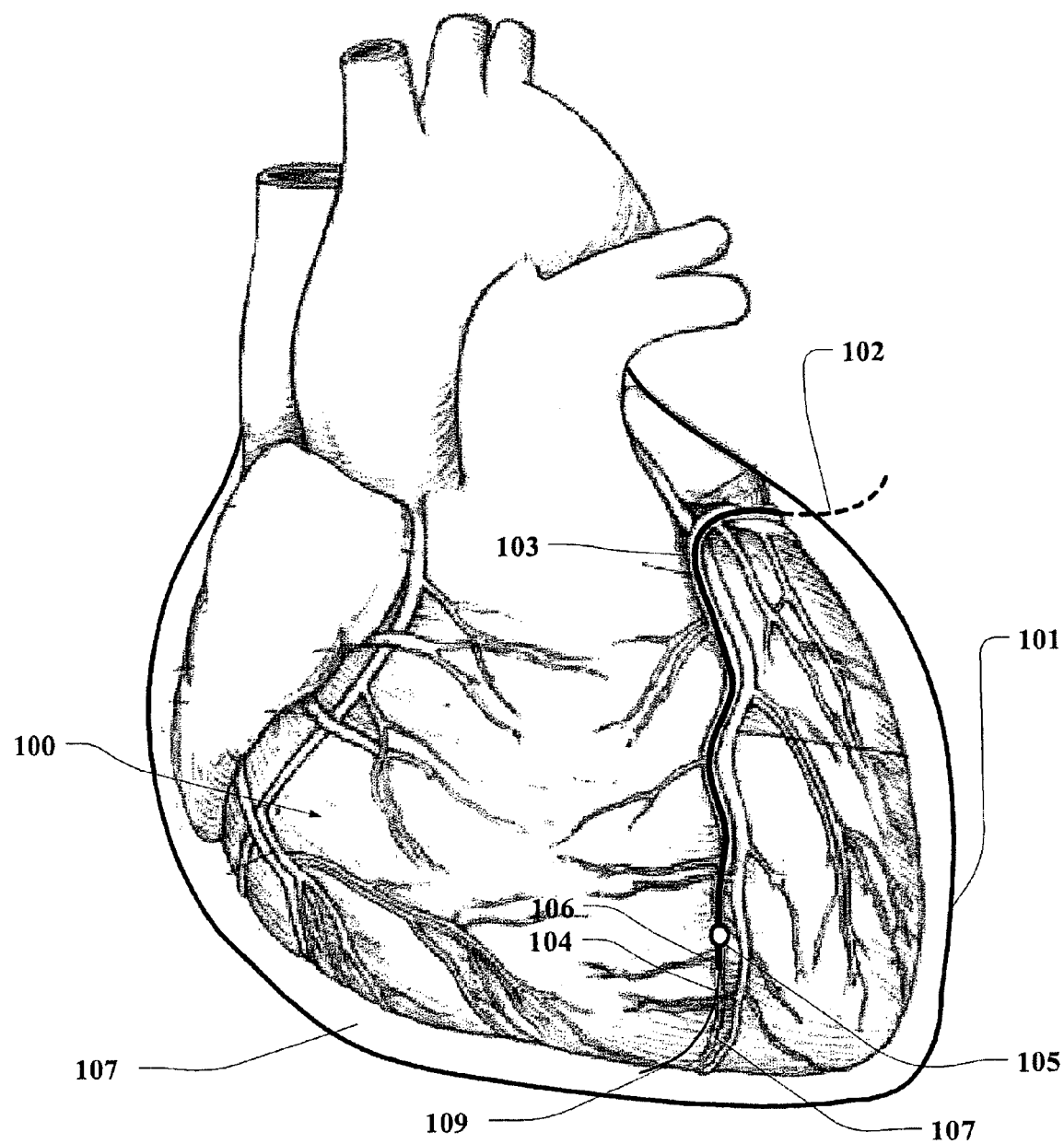
FIG. 1 is a perspective view of a distal end of a catheter inserted into a venous tree of a human heart to access the pericardial space via a distal coronary vein branch.

FIG. 1 illustrates a guiding catheter 102 in the process of accessing the pericardial space 108 formed by the heart 100 and the pericardial membrane 101, which is the outer fibrous layer of the pericardium. The catheter 102 is introduced into the coronary vein 103 through the coronary sinus of the heart (not shown). Both femoral (from below) and jugular (from the top) venous sapproaches are possible to access coronary sinus via a percutaneous puncture of a peripheral vein. These approaches are commonly used in the field of invasive cardiology. Catheters for Coronary Sinus catheterization and temporary occlusion are known in invasive cardiology. The distal catheter tip 106 is shown inside the branch 107. A smaller access device 109 is shown with its tip penetrating inside the pericardial space 108. In this preferred embodiment the access device 109 is a catheter for fluid delivery.

The catheter tip 106 has an opening for the passage of the access catheter 109. The access catheter 109 is in the fluid communication with the pericardial space. The proximal ends of the catheters 102 and 109 can be connected to various extracorporeal medical devices used to inflate and deflate the balloon 105 and for delivery and withdrawal of substances (not shown). Catheter 102 is a flexible hollow tube that can have multiple lumens inside. The balloon 105 is used to occlude the lumen of the coronary vein to isolate the distal vein branch 107. The catheter tip 106 traverses the wall of the branch 107 at the puncture point 104. It is understood that the access catheter 109 is shown as an illustration. The access can be using any therapeutic device suited for the particular therapy: an electrode lead such as an epicardial pacemaker lead with electrodes known in the field of pacemakers and cardiac pacing, a guidewire or a drug delivery catheter.

Figure 2A:
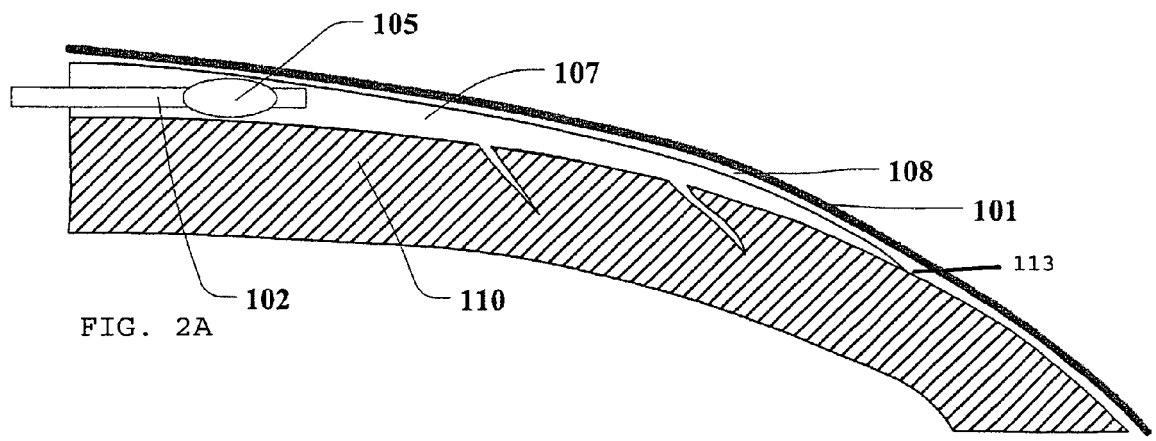
FIGS. 2A, 2B, 2C, 2D, 2E and 2F are enlarged cross-sectional views of the pericardial space to show the steps of inserting the catheter into the space (2A), inflating a balloon on the catheter to temporarily seal the space (2B), inserting an access device that can be a therapeutic device into the pericardial space between the pericardial membrane and heart muscle wall (2C), injecting a permanent sealing material in the pericardial space (2D and 2E), and removing the catheter while leaving the device in the pericardial space (2F).

FIGS. 2A to 2F illustrate the steps of the method for accessing the pericardial space using the catheter and the access device. In FIG. 2A, the guiding catheter 102 is shown inserted into the vein 103. The balloon 105 is shown deflated. The distal branch 107 of the vein 103 is not yet isolated. Pericardial membrane 101 tightly adheres to the surface of the heart muscle wall 110. The vein 103 occupies space between the membrane 101 and the heart wall 110 and is therefore inside the pericardial space.

Figure 2B:
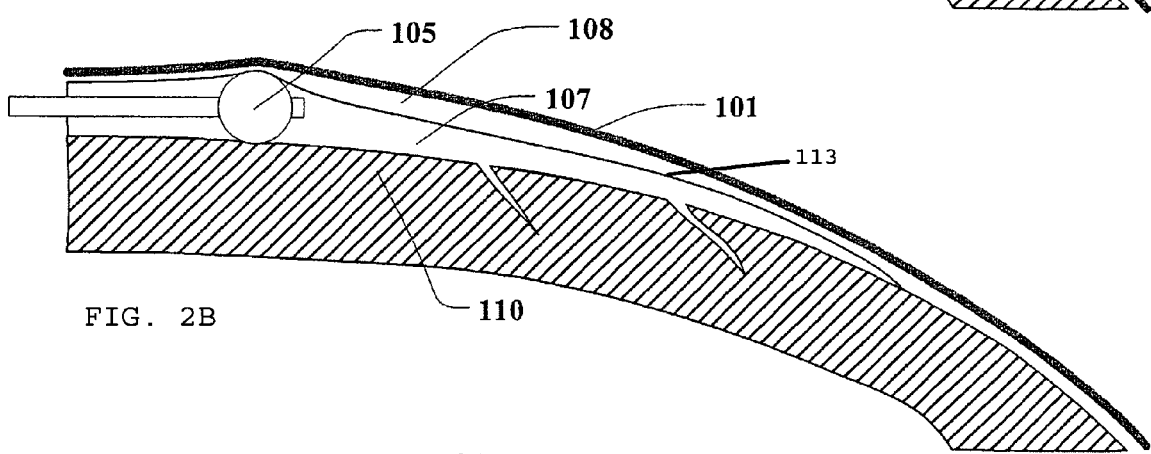

In FIG. 2B, the guiding catheter 102 is shown inserted into the vein 103. The balloon 105 is inflated. The distal branch 107 of the vein 103 is now isolated from venous circulation by the balloon. The inflation of the balloon distended the pericardial membrane 101. The membrane is less tightly adherent to the heart wall 110. The pericardial space 108 is expanded around the balloon and becomes more accessible. This local pericardial space so gained is referred to as a bubble. Physiologic fluid such as saline can be infused into the distal branch 107 at this stage of the procedure to increase the bubble size by distending the walls of the distal branch of the vein 107. The fluid can be a viscous biocompatible fluid or a gel that will not run off as quickly as saline and will allow the physician more time to take advantage of the bubble.

Figure 2C:
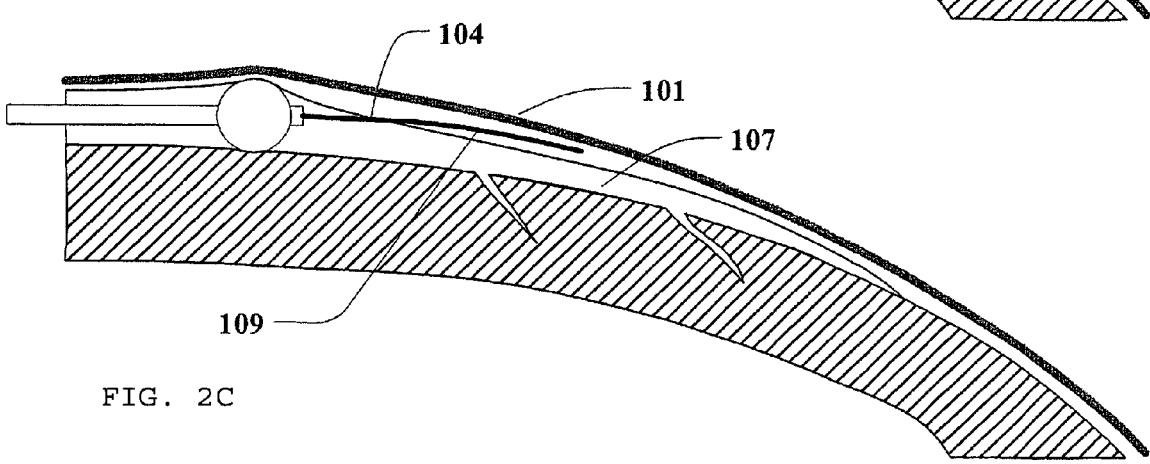

FIG. 2C shows the access device 109 puncturing the wall of the distal vein branch 107 in the puncture location 104. The access device 109 may be a flexible wire or a cannula equipped with a relatively sharp tip. The tip need not be very sharp since it is not intended to penetrate the tough pericardial membrane 101. It is only intended to puncture soft and less resilient wall of the vein and serous pericardium membrane adherent to the wall of the heart. The pericardium (also called pericardial sac or pericardial complex) consists of an outer fibrous layer 101 and an inner serous layer 113. The access device 109 need not be very resilient either, since it is expected that it will be deflected from the fibrous membrane 101. The tip of the device 109 may curl into a pigtail (not shown) after substantially exiting from the puncture to prevent accidental perforation of the pericardial membrane. It is expected that a medical imaging modality will be used to ensure that the access device is in the pericardial space and did not penetrate the chest. The physician needs not to be excessively concerned with damage to the vein 107 since at the end of the procedure it will be sacrificed and sealed.

Figure 2D:
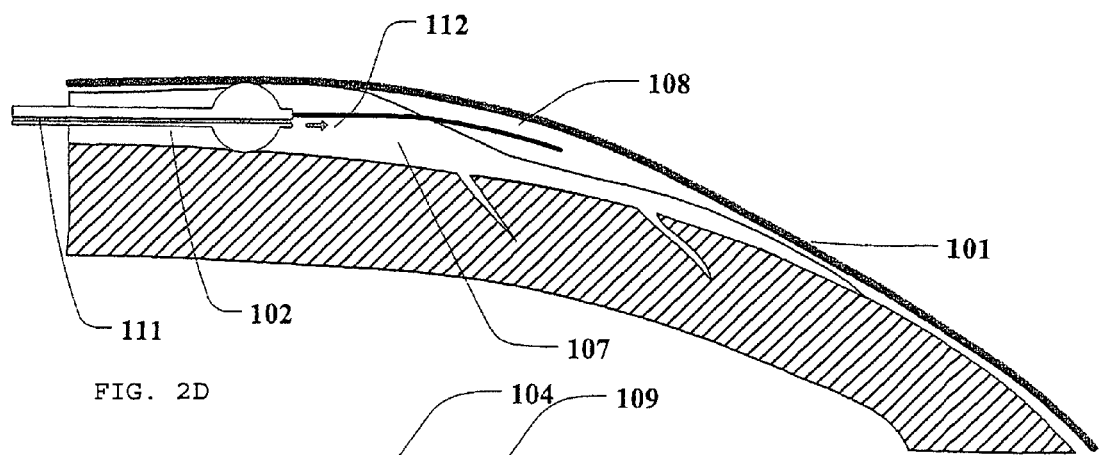

FIG. 2D shows the bubble pericardial space 108 further temporarily enlarged by the infusion of fluid 112 into the distal vein 107. The guiding catheter 102 is equipped with additional internal lumen 111 suitable for infusion of fluids.

The fluid 112 can contain a radiocontrast agent to enhance visualization of the bubble using the standard X-ray fluoroscopic technique commonly used by interventional radiologists and cardiologists. If an MRI or ultrasound visualization is used, appropriate contrast agents are also available. The purpose of this step is to further stretch and detach the membrane 101 from the heart wall.

It is understood that the access device 109 can be a guidewire and that several therapeutic devices can be introduced into the pericardial space using it as a guide. The puncture 104 can be gradually enlarged to accommodate larger devices. These "over-the-wire" exchange techniques are widely used in invasive cardiology and radiology.

Figure 2E:
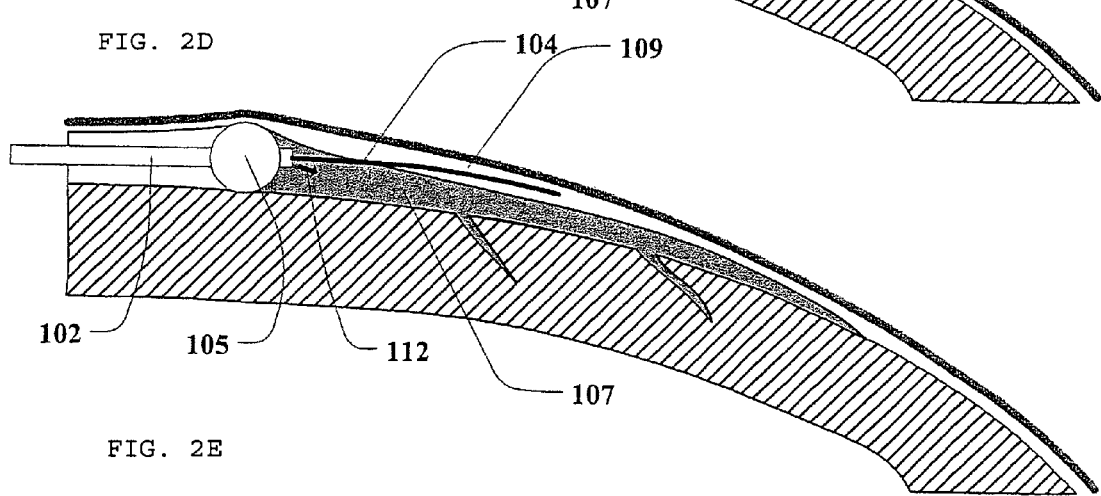

FIG. 2E shows the step of sealing the puncture site 104 in the wall of the vein 102. The access device (for example drug delivery catheter) 109 is positioned in the pericardial space and can be used to deliver therapy to the heart, but the balloon 105 is not yet deflated and the guiding catheter 102 should not be substantially pulled back yet in fear of significant bleeding. To seal the puncture a sealing agent such as for example a clotting agent or a bioglue 112 is injected into the distal vein branch 107 through the lumen 111 of the catheter 102. Alternatively the distal tip of the catheter 102 can be equipped with electrodes and RF energy can be used to cauterize and seal the distal vein 107. Alternatively heat can be delivered to the blood in the vein to clot it rapidly. Catheters to seal veins are known and used, for example, to treat veins in the legs of patients for cosmetic reasons. It can be envisioned that, after the sealing process is started, the balloon 105 is deflated and that the catheter 102 is slowly pulled back as the sealing agent is injected or the vein is sealed by the application of energy.

Figure 2F:
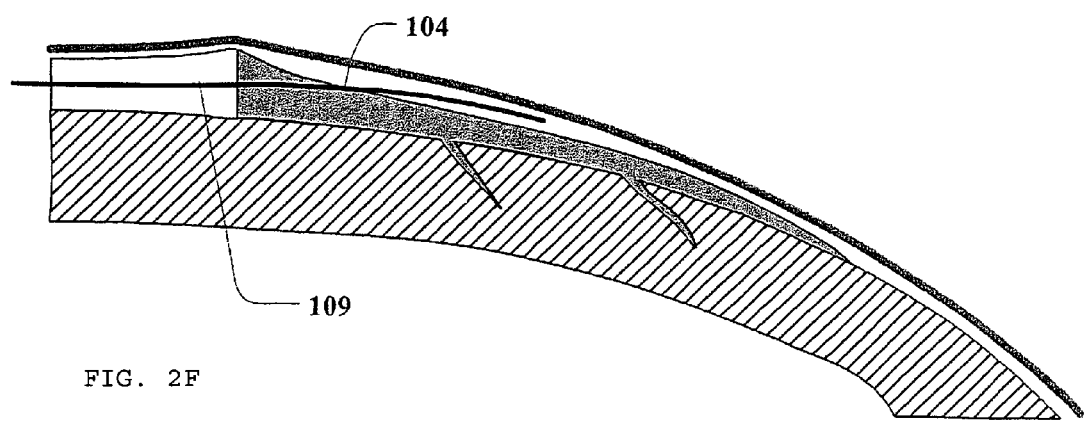

FIG. 2F shows the vein 103 after withdrawal of the introducer catheter 102. The access catheter 109 is left in place to continue therapy. It can be pulled out if needed or left in place similar to common heart pacemaker leads. The distal section of the coronary vein 104 is filled with clot and/or bioglue and will not bleed into the pericardial space.

Figure 3:
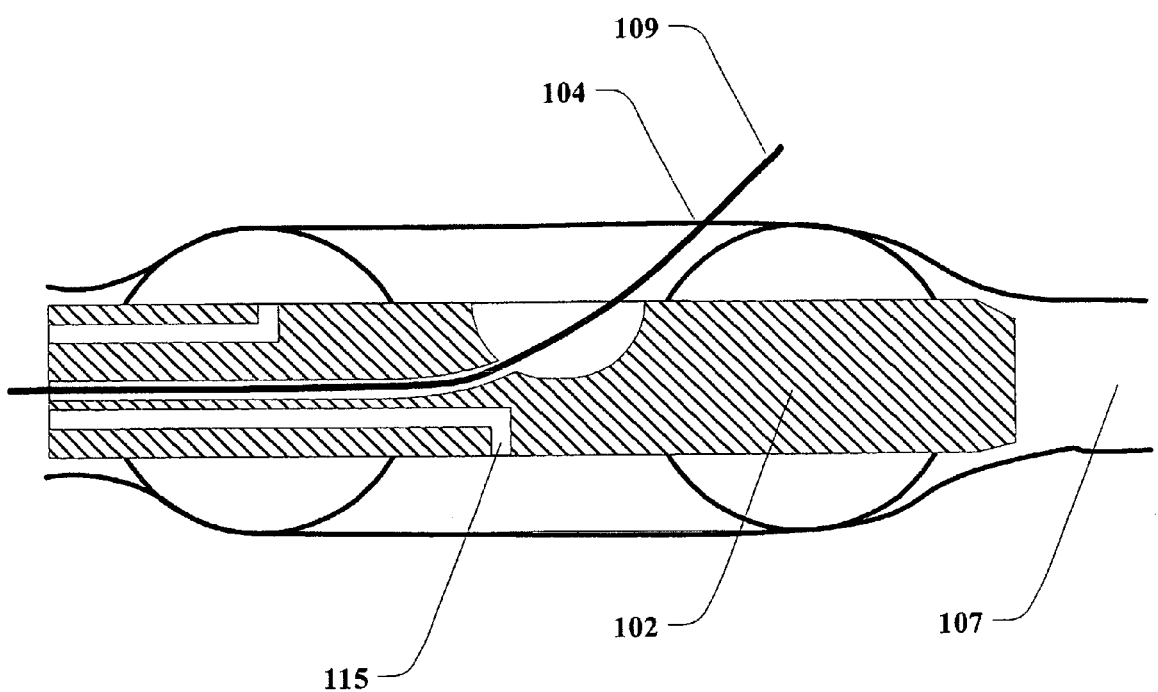
FIG. 3 illustrates an alternative embodiment of the catheter having multiple lumens (shown in cross-section) and multiple balloons wherein the catheter is inserted into the pericardial space.

FIG. 3 illustrates a more complex double balloon embodiment of the catheter distal section. The double balloon provides a high degree of isolation of the segment of the vein 107 where the puncture 104 is made to contain bleeding. In addition the dumbbell shape of the bubble space facilitates directing the access device 109 into the pericardial space. Lumen 115 can be used to infuse fluid into the isolated segment of the coronary vein and to aspirate fluid and blood if necessary.

Figure 4:
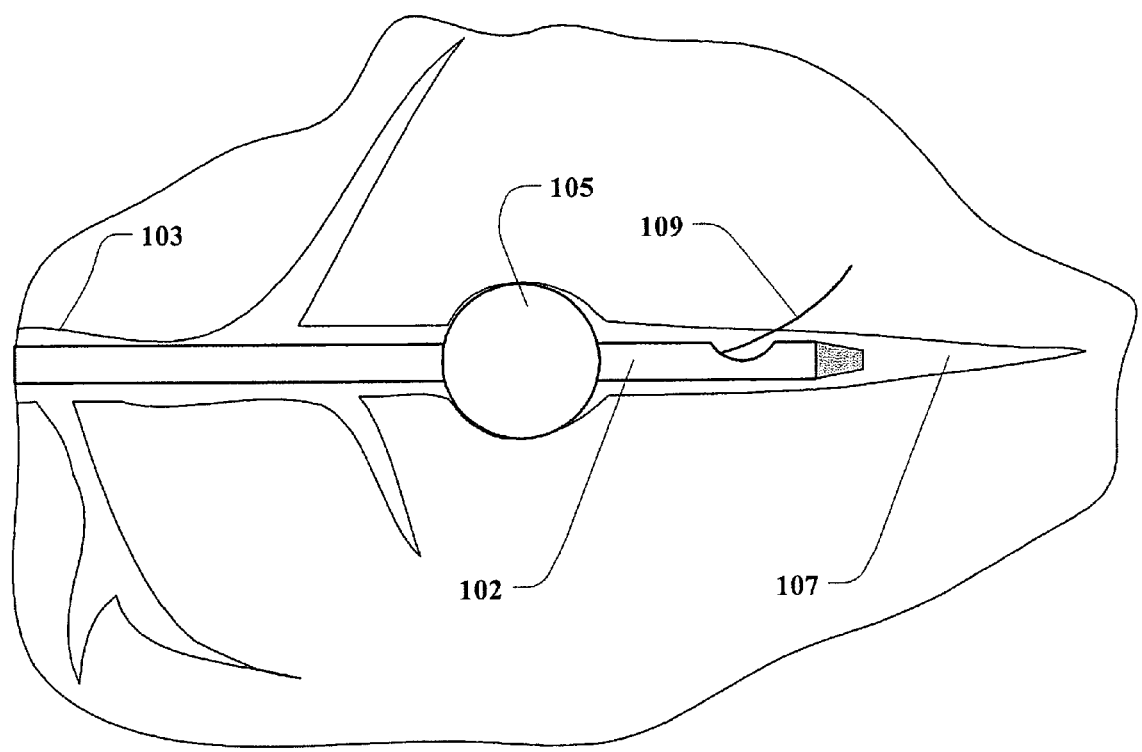
FIG. 4 is a side view of alternative catheter having a side port through which exits the access device into the pericardial space.

FIG. 4 is a side view of catheter 102 in the coronary vein 103, and shows a view orthogonal to the view plane of FIGS. 2A to F. The access device 109 exits the guiding catheter 102 sideways using a side opening in the catheter shaft. This exit direction facilitates directing and positioning of the access device 109.

The invention has been described in connection with the best mode now known to the applicant inventors. The invention is not to be limited to the disclosed embodiment. Rather, the invention covers all of various modifications and equivalent arrangements included within the spirit and scope of the appended claims. Common to all the embodiments is that access is gained into the pericardial space of a patient by puncturing and then sealing a branch of a cardiac vein.

What is claimed is:

1. A method for accessing a pericardial space of a heart of a mammalian patient comprising:
    Guiding a catheter through a coronary sinus of the heart and to a cardiac vein which is distal to the coronary sinus;
    Advancing said catheter to a distal segment of the cardiac vein and further comprising sacrificing the distal segment of vein due to an occlusion resulting from the catheter;
    Intentionally puncturing the vein with the catheter to access the pericardial space;
    Performing a therapy or a diagnostic procedure in the pericardial space using the catheter and the puncture in the vein, wherein the therapy or diagnostic procedure includes at least one of delivery drugs to the pericardial space, delivery of a genetic agent to the pericardial space placement of electrodes into the pericardial space, removal of fluid from the pericardial space and infusion of fluid into the pericardial space, and
    Durably sealing the distal segment with the catheter.

2. The method of claim 1 further comprising extending an access device of the catheter through the puncture and into the pericardial space.

3. The method of claim 1 further comprising delivering the therapy to the pericardial space through the catheter and the puncture.

4. The method of claim 1 farther comprising temporary sealing the distal segment by expanding a balloon at a distal end of the catheter and thereafter puncturing the vein.

5. A method for accessing a pericardial space of a heart of a mammalian patient comprising:
    Guiding a catheter through a coronary sinus of the heart and to a cardiac vein which is distal to the coronary sinus;
    Advancing said catheter to the cardiac vein;
    Intentionally puncturing the vein with the catheter to access the pericardial space, and performing a therapy or a diagnostic procedure in the pericardial space using the catheter and the puncture in the vein further comprising permanently sealing a distal segment of the cardiac vein.

6. The method of claim 5 further comprising sealing the vein by at least one of infusion of bioglue, infusion of a clotting agent, delivery of heat, and delivery of RF energy.

7. The method of claim 1 further comprising expanding an expandable device at a distal section of the catheter to distend the cardiac vein and thereafter extending an access device from the catheter to puncture the cardiac vein and a serous layer of a pericardium which includes the pericardium space.

8. A method for transvenously accessing a pericardial space between a serous layer and a fibrous layer of a pericardium of a heart in a mammalian patient, said method comprising:
    guiding a catheter through a coronary vein to a region adjacent the pericardial space;
    intentionally accessing the pericardial space with the catheter by penetrating the coronary vein and the serous layer;
    performing a therapy within the pericardial space using the catheter in the pericardial space, and
    sealing coronary vein, wherein the seal is a permanent seal of a distal segment of the coronary vein, wherein the catheter extends to the distal segment and is retracted from the patient after sealing the distal segment, and the permanent seal causes the distal segments to be sacrificed.

9. The method of claim 8 wherein the catheter is guided through a coronary sinus to a distal segment of a coronary vein and the distal segment is penetrated to access the pericardial space.

10. The method of claim 8 wherein the seal is a temporary seal formed by expanding a distal section of the catheter in the coronary vein to occlude the distal segment of the coronary vein, and the temporary seal is applied before accessing the pericardial space.

11. The method of claim 8 wherein permanent seal is achieved by at least one of infusion of bioglue, infusion of a clotting agent, delivery of heat, and delivery of RF energy.

12. The method of claim 8 farther comprising extending an access device of the catheter through the puncture and into the pericardial space, and farther comprising providing fluid communication between the pericardial space and an internal lumen of the catheter.

13. The method of claim 8 wherein the pericardial space is accessed by extending an access device from the catheter between a serous layer and fibrous layer of a pericardium of the heart.

14. The method of claim 13 wherein the serous layer and fibrous layers are separated by distending a distal segment of the coronary vein with the catheter.

15. The method of claim 14 wherein a balloon on the catheter distends the distal segment.

* * * * *